United States Patent
Fukuchi et al.

(10) Patent No.: US 11,965,843 B2
(45) Date of Patent: Apr. 23, 2024

(54) CHEMICAL BOND EVALUATION METHOD WITH A MULTIDIMENSIONAL SOLID-STATE NUCLEAR MAGNETIC RESONANCE (NMD) ANALYSIS

(71) Applicant: SUMITOMO RUBBER INDUSTRIES, LTD., Kobe (JP)

(72) Inventors: Masashi Fukuchi, Kobe (JP); Takehiro Kitaura, Kobe (JP); Hiroaki Yamada, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 0 days.

(21) Appl. No.: 17/888,654

(22) Filed: Aug. 16, 2022

(65) Prior Publication Data
US 2023/0077190 A1 Mar. 9, 2023

(30) Foreign Application Priority Data

| Sep. 2, 2021 | (JP) | 2021-143181 |
| Jun. 13, 2022 | (JP) | 2022-095163 |
| Jul. 6, 2022 | (JP) | 2022-109025 |

(51) Int. Cl.
| *G01N 24/08* | (2006.01) |
| *G01N 33/44* | (2006.01) |
| *C08K 9/06* | (2006.01) |

(52) U.S. Cl.
CPC .......... *G01N 24/08* (2013.01); *G01N 33/445* (2013.01); *C08K 9/06* (2013.01)

(58) Field of Classification Search
None
See application file for complete search history.

(56) References Cited

U.S. PATENT DOCUMENTS

2004/0266968 A1* 12/2004 Korth .................. C07F 7/1804
556/427

FOREIGN PATENT DOCUMENTS

| JP | 2006-337342 A | 12/2006 |
| JP | 2010-216952 A | 9/2010 |
| JP | 2013108845 A * | 6/2013 |

OTHER PUBLICATIONS

Lee et al., Untangling the Condensation Network of Organosiloxanes on Nanoparticles using 2D 29Si-29Si Solid-State NMR Enhanced by Dynamic Nuclear Polarization; Aug. 2014, American Chemical Society; pp. 13781-13788.*

* cited by examiner

*Primary Examiner* — Jay Patidar
(74) *Attorney, Agent, or Firm* — Birch, Stewart, Kolasch & Birch, LLP

(57) ABSTRACT

A chemical bond evaluation method capable of directly evaluating the presence or absence of a chemical bond between silica and a silane coupling agent includes performing multidimensional solid-state nuclear magnetic resonance (NMR) analysis on a rubber composition comprising a rubber component, a silica, and a silane coupling agent; and evaluating the presence or absence of a chemical bond between silica and the silane coupling agent in the rubber composition containing a rubber component, the silica, and the silane coupling agent.

3 Claims, 2 Drawing Sheets

CHEMICAL BOND EVALUATION METHOD WITH A MULTIDIMENSIONAL SOLID-STATE NUCLEAR MAGNETIC RESONANCE (NMD) ANALYSIS

TECHNICAL FIELD

The present disclosure relates to a chemical bond evaluation method.

BACKGROUND ART

It has been known to blend silica as a reinforcing filler for the purposes such as less heat build-up in rubber compositions. It has been further proposed to combine a silane coupling agent in order to improve dispersion of silica. In such silica blends, the formation of a bond via a silane coupling agent, i.e., a silica-silane coupling agent-polymer bond is considered to be important and may be confirmed using techniques such as $^{29}$Si solid-state NMR analysis.

For example, Patent Literatures 1 and 2 disclose methods of using $^{29}$Si solid-state NMR analysis to evaluate the reaction of a silane coupling agent in a silica blend or to determine the amount of reaction between silica and a silane coupling agent.

CITATION LIST

Patent Literature

Patent Literature 1: JP 2010-216952 A
Patent Literature 2: JP 2006-337342 A

SUMMARY OF DISCLOSURE

Technical Problem

However, the methods of Patent Literatures 1 and 2 can only quantify the amount of reaction between silica and a silane coupling agent and cannot directly evaluate whether or not a chemical bond is formed between the silica and silane coupling agent.

The present disclosure aims to solve the above problem and provide a chemical bond evaluation method capable of directly evaluating the presence or absence of a chemical bond between silica and a silane coupling agent.

Solution to Problem

The present disclosure relates to a chemical bond evaluation method including evaluating the presence or absence of a chemical bond between silica and a silane coupling agent in a rubber composition containing a rubber component, the silica, and the silane coupling agent.

Advantageous Effects of Disclosure

The chemical bond evaluation method according to the present disclosure includes evaluating the presence or absence of a chemical bond between silica and a silane coupling agent in a rubber composition containing a rubber component, the silica, and the silane coupling agent. This method enables direct evaluation of the presence or absence of the chemical bond.

DESCRIPTION OF EMBODIMENTS

Figure 1:
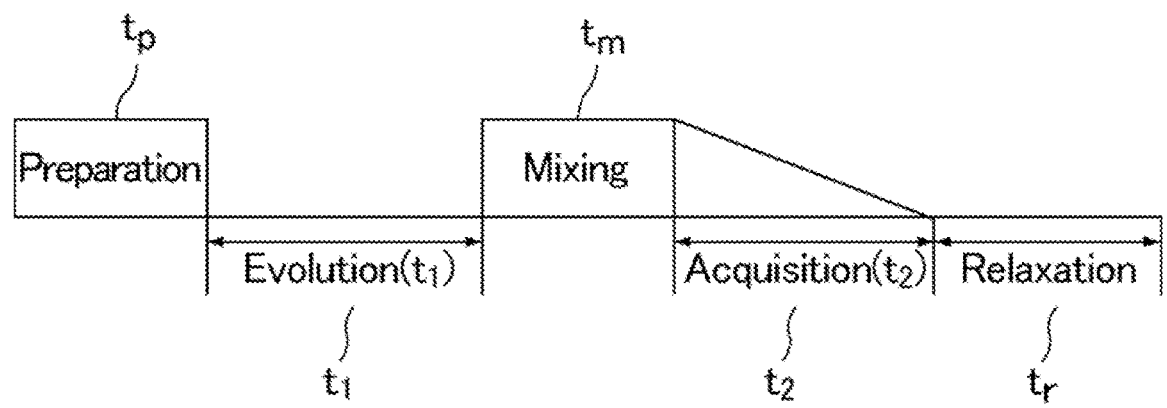
FIG. 1 is a block diagram of a pulse sequence used for 2D NMR analysis.

The present disclosure provides a chemical bond evaluation method including evaluating the presence or absence of a chemical bond between silica and a silane coupling agent in a rubber composition containing a rubber component, the silica, and the silane coupling agent.

In the one-dimensional nuclear magnetic resonance methods (1D NMR) disclosed in Patent Literatures 1 and 2, for example, the amount of silica in a state not chemically bonded to a silane coupling agent is much larger, while the peak of silica in a bonded state is buried in the spectrum, and thus the silica-silane coupling agent chemical bond cannot be directly evaluated. In contrast, according to the present disclosure, techniques such as multidimensional nuclear magnetic resonance (multidimensional NMR) may be used to establish a method for evaluating the presence or absence of a chemical bond between silica and a silane coupling agent, which has not been able to be evaluated so far. Thus, the present disclosure enables direct evaluation of the presence or absence of a chemical bond between silica and a silane coupling agent in a rubber composition containing the silica and the silane coupling agent.

In the chemical bond evaluation method, the rubber composition to be evaluated contains a rubber component, silica, and a silane coupling agent.

The rubber component used may be, for example, a diene rubber. Examples of diene rubbers include isoprene-based rubbers, polybutadiene rubbers (BR), styrene-butadiene rubbers (SBR), styrene-isoprene-butadiene rubbers (SIBR), ethylene-propylene-diene rubbers (EPDM), chloroprene rubbers (CR), and acrylonitrile-butadiene rubbers (NBR). The examples also include butyl-based rubbers and fluororubbers. For example, SBR, BR, and isoprene-based rubbers can be suitably used in tire applications. These may be used alone or in combinations of two or more.

The diene rubbers may be either unmodified or modified diene rubbers.

The modified diene rubbers may be any diene rubber having a functional group interactive with filler such as silica. Examples include a chain end-modified diene rubber obtained by modifying at least one chain end of a diene rubber with a compound (modifier) having the functional group (i.e., a chain end-modified diene rubber terminated with the functional group); a backbone-modified diene rubber having the functional group in the backbone; a backbone- and chain end-modified diene rubber having the functional group in both the backbone and chain end (e.g., a backbone- and chain end-modified diene rubber in which the backbone has the functional group and at least one chain end is modified with the modifier); and a chain end-modified diene rubber into which a hydroxy or epoxy group has been introduced by modification (coupling) with a polyfunctional compound having two or more epoxy groups in the molecule.

Examples of the functional group include amino, amide, silyl, alkoxysilyl, isocyanate, imino, imidazole, urea, ether, carbonyl, oxycarbonyl, mercapto, sulfide, disulfide, sulfonyl, sulfinyl, thiocarbonyl, ammonium, imide, hydrazo, azo, diazo, carboxy, nitrile, pyridyl, alkoxy, hydroxy, oxy, and epoxy groups. These functional groups may be substituted. For example, preferred are amino (preferably amino whose hydrogen atom is replaced with a C1-C6 alkyl group), alkoxy (preferably C1-C6 alkoxy), and alkoxysilyl (preferably C1-C6 alkoxysilyl) groups.

Any SBR may be used, including for example emulsion-polymerized styrene-butadiene rubbers (E-SBR) and solution-polymerized styrene-butadiene rubbers (S-SBR). These may be used alone or in combinations of two or more. The SBR may be either unmodified or modified SBR. Examples of the modified SBR include those into which functional groups as listed for the modified diene rubbers have been introduced.

The amount of SBR, if present, based on 100% by mass of the rubber component content in the rubber composition is not limited and is, for example, preferably 10% by mass or more, more preferably 20% by mass or more, and may be 100% by mass.

Any BR may be used, including for example high-cis BR having a high cis content, BR containing syndiotactic polybutadiene crystals, and BR synthesized using rare earth catalysts (rare earth-catalyzed BR). These may be used alone or in combinations of two or more. The BR may be either unmodified or modified BR. Examples of the modified BR include those into which functional groups as listed for the modified diene rubbers have been introduced.

The amount of BR, if present, based on 100% by mass of the rubber component content in the rubber composition is not limited and is, for example, preferably 10% by mass or more, more preferably 20% by mass or more. The upper limit of the amount is preferably 90% by mass or less, more preferably 80% by mass or less.

Examples of isoprene-based rubbers include natural rubbers (NR), polyisoprene rubbers (IR), refined NR, modified NR, and modified IR. Examples of NR include those commonly used in the rubber industry such as SIR20, RSS #3, and TSR20. Any IR may be used, including for example those commonly used in the rubber industry, such as IR2200. Examples of the refined NR include deproteinized natural rubbers (DPNR) and highly purified natural rubbers (UPNR). Examples of the modified NR include epoxidized natural rubbers (ENR), hydrogenated natural rubbers (HNR), and grafted natural rubbers. Examples of the modified IR include epoxidized polyisoprene rubbers, hydrogenated polyisoprene rubbers, and grafted polyisoprene rubbers. These may be used alone or in combinations of two or more.

The amount of isoprene-based rubbers, if present, based on 100% by mass of the rubber component content in the rubber composition is not limited and is, for example, preferably 10% by mass or more, more preferably 20% by mass or more. The upper limit of the amount is preferably 90% by mass or less, more preferably 80% by mass or less.

Any silica may be used, and examples include dry silica (anhydrous silica) and wet silica (hydrous silica). These may be used alone or in combinations of two or more.

The amount of silica per 100 parts by mass of the rubber component content is not limited and is, for example, preferably 20 parts by mass or more, more preferably 30 parts by mass or more, still more preferably 50 parts by mass or more. The upper limit of the amount is not limited, but is preferably 300 parts by mass or less, more preferably 200 parts by mass or less, still more preferably 150 parts by mass or less. When the amount is equal to or less than the upper limit, good dispersion tends to be obtained.

The nitrogen adsorption specific surface area ($N_2SA$) of the silica is not limited and is, for example, preferably 70 $m^2/g$ or more, more preferably 140 $m^2/g$ or more, still more preferably 160 $m^2/g$ or more. The upper limit of the $N_2SA$ of the silica is not limited, but is preferably 500 $m^2/g$ or less, more preferably 300 $m^2/g$ or less, still more preferably 250 $m^2/g$ or less.

Here, the $N_2SA$ of the silica is measured by a BET method in accordance with ASTM D3037-93.

Any silane coupling agent may be used, and examples include sulfide silane coupling agents such as bis(3-triethoxysilylpropyl) tetrasulfide, bis(2-triethoxysilylethyl)tetrasulfide, bis(4-triethoxysilylbutyl)tetrasulfide, bis(3-trimethoxysilylpropyl)tetrasulfide, bis(2-trimethoxysilylethyl) tetrasulfide, bis(2-triethoxysilylethyl)trisulfide, bis(4-trimethoxysilylbutyl)trisulfide, bis(3-triethoxysilylpropyl) disulfide, bis(2-triethoxysilylethyl)disulfide, bis(4-triethoxysilylbutyl)disulfide, bis(3-trimethoxysilylpropyl) disulfide, bis(2-trimethoxysilylethyl)disulfide, bis(4-trimethoxysilylbutyl)disulfide, 3-trimethoxysilylpropyl-N,N-dimethylthiocarbamoyltetrasulfide, 2-triethoxysilylethyl-N,N-dimethylthiocarbamoyltetrasulfide, and 3-triethoxysilylpropyl methacrylate monosulfide; mercapto silane coupling agents such as 3-mercaptopropyltrimethoxysilane, 2-mercaptoethyltriethoxysilane, and NXT and NXT-Z both available from Momentive; vinyl silane coupling agents such as vinyltriethoxysilane and vinyltrimethoxysilane; amino silane coupling agents such as 3-aminopropyltriethoxysilane and 3-aminopropyltrimethoxysilane; glycidoxy silane coupling agents such as γ-glycidoxypropyltriethoxysilane and γ-glycidoxypropyltrimethoxysilane; nitro silane coupling agents such as 3-nitropropyltrimethoxysilane and 3-nitropropyltriethoxysilane; and chloro silane coupling agents such as 3-chloropropyltrimethoxysilane and 3-chloropropyltriethoxysilane. These may be used alone or in combinations of two or more.

The amount of silane coupling agents per 100 parts by mass of the silica content in the rubber composition is not limited and is, for example, preferably 3 parts by mass or more, more preferably 6 parts by mass or more. The amount is also preferably 20 parts by mass or less, more preferably 15 parts by mass or less.

The rubber composition may contain other fillers in addition to silica. Examples of such other fillers include fillers known in the rubber field, such as carbon black, calcium carbonate, talc, alumina, clay, aluminum hydroxide, aluminum oxide, and mica.

The rubber composition preferably contains a vulcanizing agent from the standpoint of rubber properties.

Any vulcanizing agent may be used, and examples include sulfur. Examples of the sulfur include those commonly used in the rubber industry, such as powdered sulfur, precipitated sulfur, colloidal sulfur, insoluble sulfur, highly dispersible sulfur, and soluble sulfur. These may be used alone or in combinations of two or more.

The amount of sulfur per 100 parts by mass of the rubber component content in the rubber composition is not limited and is, for example, preferably 0.1 parts by mass or more, more preferably 0.5 parts by mass or more, still more preferably 0.7 parts by mass or more. The amount is preferably 6.0 parts by mass or less, more preferably 4.0 parts by mass or less, still more preferably 3.0 parts by mass or less.

The rubber composition preferably contains a vulcanization accelerator from the standpoint of rubber properties.

Any type of vulcanization accelerator may be used, including usual vulcanization accelerators. Examples of the vulcanization accelerators include: thiazole vulcanization accelerators such as 2-mercaptobenzothiazole, di-2-benzothiazolyl disulfide, and N-cyclohexyl-2-benzothiazylsulfenamide; thiuram vulcanization accelerators such as tetramethylthiuram disulfide (TMTD), tetrabenzylthiuram disulfide (TBzTD), and tetrakis(2-ethylhexyl)thiuram disulfide TOT-N); sulfenamide vulcanization accelerators such as N-cyclohexyl-2-benzothiazole sulfenamide, N-t-butyl-2-benzothiazolylsulfenamide, N-oxyethylene-2-benzothiazole sulfenamide, and N,N'-diisopropyl-2-benzothiazole sulfenamide; and guanidine vulcanization accelerators such as diphenylguanidine, diorthotolylguanidine, and orthotolylbiguanidine. These may be used alone or in combinations of two or more.

The amount of vulcanization accelerators per 100 parts by mass of the rubber component content in the rubber composition is not limited and is usually 0.3 to 10 parts by mass, preferably 0.5 to 7 parts by mass.

The rubber composition may contain compounding agents other than the components described above.

Examples of such other compounding agents include materials known in the rubber field, such as plasticizers (e.g., oils, liquid resins, solid resins), antioxidants, stearic acid, zinc oxide, waxes, release agents, and pigments. The compounding agents to be used and the amounts thereof may be appropriately selected depending on the intended use and other factors.

The rubber composition may be either an unvulcanized rubber composition (rubber composition before vulcanization) or a vulcanized rubber composition (rubber composition after vulcanization), or may include both.

The rubber composition can be prepared by known methods. For example, the components may be kneaded in a rubber kneading machine such as an open roll mill or a Banbury mixer to prepare an unvulcanized rubber composition, which may then be crosslinked (vulcanized) to prepare a vulcanized rubber composition.

The chemical bond evaluation method evaluates the above-described rubber composition (sample) containing a rubber component, silica, a silane coupling agent, and other components with respect to the presence or absence of a chemical bond between the silica and silane coupling agent contained in the rubber composition. Here, the presence or absence of the chemical bond may be evaluated by, for example, solid-state nuclear magnetic resonance (solid-state NMR). In particular, multidimensional solid-state nuclear magnetic resonance (multidimensional solid-state NMR) is desirable from the standpoint of evaluating the presence or absence of a chemical bond between silica and a silane coupling agent.

An NMR apparatus is an analyzer which irradiates a predetermined atomic nucleus in a sample placed in a static magnetic field with a radio frequency magnetic field pulse and detects an NMR signal from the predetermined atomic nucleus after a predetermined period of time. In the recent years, multidimensional NMR analysis has been widely used in NMR spectroscopy. The multidimensional NMR analysis has the advantage that NMR signals may be displayed in a frequency space having two or more frequency axes, which improves resolution and facilitates spectral analysis compared to 1D NMR analysis, thereby enabling elucidation of the interaction between nuclear spins.

Figure 2:
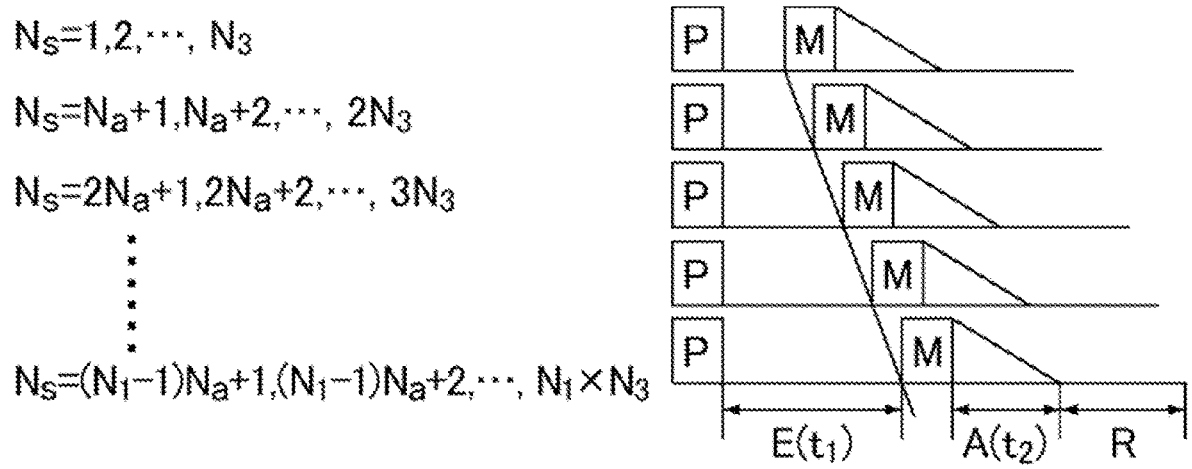
FIG. 2 is a conceptual diagram of 2D NMR analysis.

FIG. 1 and FIG. 2 show conceptual diagrams of 2D NMR analysis as an example of multidimensional NMR analysis. Three or more dimensional analysis is an extension of 2D analysis and does not have a new concept, and thus a separate description thereof will be omitted. FIG. 1 shows the general constitution of a pulse sequence used in 2D NMR analysis (hereinafter referred to as "2D pulse sequence"). The 2D pulse sequence is constituted by five periods including a preparation period (Preparation), an evolution period (Evolution), a mixing period (Mixing), an acquisition period (Acquisition), and a relaxation period (Relaxation).

Among the five periods, the preparation period and the mixing period each include irradiation with one or more magnetic field pulses. The evolution period is a delay time from the preparation period to the mixing period, which is usually denoted as $t_1$ and called the evolution period. The acquisition period is a period in which an NMR signal may be acquired by a reception system, and is usually denoted as $t_2$. In general, the execution of a pulse sequence with one acquisition period is referred to as a scan, which is a unit for measuring the number of NMR analyses. The relaxation period is a waiting time (period) until the atomic nucleus returns to a state before irradiation with the pulse sequence.

The 2D NMR analysis is accomplished by repeating the 2D pulse sequence while varying the evolution period $t_1$. FIG. 2 is a conceptual diagram thereof. Ns is the number of scans, and scanning using the pulse sequence with a fixed evolution period $t_1$ is repeated Na times. All the acquired NMR signals are accumulated in a reception processor. Thus, Na is referred to as the number of accumulations. After Na scans are completed, the evolution period $t_1$ is increased by an increment $\Delta t_1$ previously input by the user, and Na scans are performed again. The 2D NMR analysis is accomplished by repeating this process until the evolution period $t_1$ is increased for the number of times previously input by the user, $Nt_1$ times.

The NMR analysis performed as described above provides an NMR spectrum.

$^{29}$Si solid-state nuclear magnetic resonance is preferably used in at least one dimension of the multidimensional solid-state nuclear magnetic resonance (multidimensional solid-state NMR). As long as $^{29}$Si solid-state nuclear magnetic resonance is used in at least one dimension, any technique may be used in the other dimensions. Exemplary techniques include $^1$H solid-state nuclear magnetic resonance and $^{13}$C solid-state nuclear magnetic resonance. For example, when $^{13}$C solid-state nuclear magnetic resonance is used, it is possible to evaluate direct bonding to $^{13}$C.

Moreover, the multidimensional solid-state nuclear magnetic resonance (multidimensional solid-state NMR) used may be multidimensional $^{29}$Si solid-state NMR analysis (solid-state high-resolution $^{29}$Si NMR analysis). The $^{29}$Si solid-state NMR analysis used may be $^{29}$Si DD/MAS NMR analysis (DD/MAS method) or $^{29}$Si CP/MAS NMR analysis (CP/MAS method). Here, the DD/MAS method refers to the dipolar decoupling/magic angle spinning method, and the CP/MAS method refers to the cross polarization/magic angle spinning method.

Figure 3:
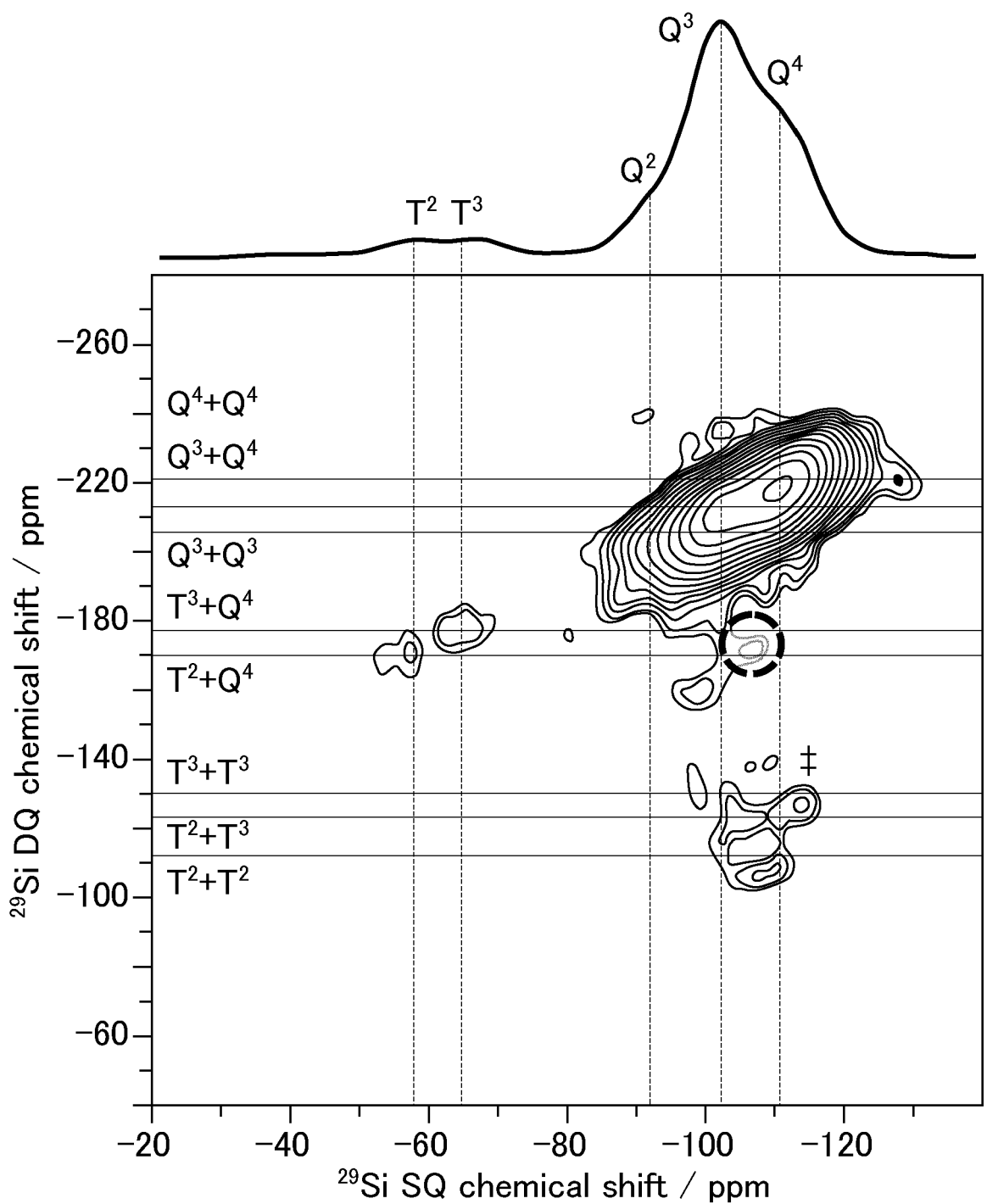
FIG. 3 shows an example of a 2D $^{29}$Si-$^{29}$Si homonuclear solid-state nuclear magnetic resonance spectrum.

The multidimensional $^{29}$Si solid-state NMR analysis may be performed on the rubber composition (sample) to obtain, for example, a 2D $^{29}$Si-$^{29}$Si homonuclear solid-state nuclear magnetic resonance spectrum as shown in FIG. 3. In the spectrum, the vertical axis represents a $^{29}$Si DQ chemical shift axis and the horizontal axis represents a $^{29}$Si SQ chemical shift axis.

The spectrum assignment is as described in Patent Literature 2 and Udo Goerl et al., "Investigations Into The Silica/Silane Reaction System", Rubber Chemistry And Technology, Vol. 70, pp. 608-623, 1997. The peak at around −85 to −95 ppm indicates the Q2 structure (a Si atom bonded to two OH groups), the peak at around −96 to −105 ppm indicates the Q3 structure (a Si atom bonded to one OH group), and the peak at around −106 to −115 ppm indicates the Q4 structure (a Si atom bonded to no OH group).

Then, the cross peak indicated by the circle (broken line) in FIG. 3 is assigned to silica in a state forming a chemical bond with a silane coupling agent. Thus, the 2D $^{29}$Si-$^{29}$Si homonuclear solid-state nuclear magnetic resonance spectrum in FIG. 3 shows that it is possible to directly observe silica in a state chemically bonded to a silane coupling agent. On the other hand, in the upper part of FIG. 3, which corresponds to the 1D NMR analysis of the same rubber composition (sample), it is impossible to directly observe silica in a state chemically bonded to a silane coupling agent because the peak of Q4' located between Q3 and Q4 is much smaller than any other peak assigned to silicon and thus is inseparably buried.

As described above, FIG. 3 specifically shows that it is possible to directly observe Q4' (silica in a state bonded to a silane coupling agent), for example, by performing multidimensional solid-state NMR such as 2D solid-state NMR as a method for evaluating the presence or absence of a chemical bond between silica and a silane coupling agent in a rubber composition (sample).

Here, the rubber composition (sample) is not limited, and applicable examples include rubber compositions for use in tire components. Examples of the tire components include treads (cap treads), sidewalls, base treads, undertreads, shoulders, clinches, bead apexes, breaker cushion rubbers, rubbers for carcass cord topping, insulations, chafers, and innerliners.

Examples of tires including the tire components include tires for passenger vehicles, tires for large passenger vehicles, tires for large SUVs, tires for trucks and buses, tires for two-wheeled vehicles, racing tires, winter tires (studless winter tires, snow tires, cold weather tires, studded tires), all season tires, run-flat tires, aircraft tires, and mining tires.

EXAMPLES

The present disclosure will be specifically described with reference to, but not limited to, examples.

The chemicals used in the example and comparative example are listed below.
SBR: NS616 (non-oil extended SBR) available from Zeon Corporation.
Silica: Ultrasil VN3 ($N_2$SA 175 m$^2$/g) available from Evonik-Degussa
Silane coupling agent: Si266 (bis(3-triethoxysilylpropyl) disulfide) available from Evonik-Degussa
Oil: Diana Process NH-70S (aromatic process oil) available from Idemitsu Kosan Co., Ltd.
Wax: Ozoace 0355 available from Nippon Seiro Co., Ltd.
Antioxidant: NOCRAC 6C (N-(1,3-dimethylbutyl)-N'-phenyl-p-phenylenediamine) available from Ouchi Shinko Chemical Industrial Co., Ltd.
Zinc oxide: zinc oxide #1 available from Mitsui Mining & Smelting Co., Ltd.
Stearic acid: stearic acid "TSUBAKI" available from NOF Corporation
Sulfur: HK-200-5 (5 wt % oil-containing powdered sulfur) available from Hosoi Chemical Industry Co., Ltd.
Vulcanization accelerator CZ: NOCCELER CZ (N-cyclohexyl-2-benzothiazolylsulfenamide) available from Ouchi Shinko Chemical Industrial Co., Ltd.
Vulcanization accelerator DPG: NOCCELER D (diphenylguanidine) available from Ouchi Shinko Chemical Industrial Co., Ltd.
(Preparation of Rubber Composition (Vulcanized))

In accordance with the blend recipe shown in Table 1, the materials other than the sulfur and vulcanization accelerators were kneaded for five minutes at 150° C. using a 1.7 L Banbury mixer (Kobe Steel, Ltd.) to give a kneaded mixture. Next, the sulfur and vulcanization accelerators were added to the kneaded mixture, and they were kneaded using an open roll mill for five minutes at 80° C. to obtain an unvulcanized rubber composition. The unvulcanized rubber composition was press-vulcanized for 12 minutes at 150° C. to obtain a vulcanized rubber composition (sample).

TABLE 1

| Rubber composition (vulcanized) | |
| --- | --- |
| SBR | 100 |
| Silica | 100 |
| Silane coupling agent | 8 |
| Oil | 4 |
| Wax | 2 |
| Antioxidant | 2 |
| Zinc oxide | 2 |
| Stearic acid | 2 |
| Sulfur | 1.5 |
| Vulcanization accelerator CZ | 2 |
| Vulcanization accelerator DPG | 2 |

Unit: parts by mass

Comparative Example

Normal solid-state NMR analysis was performed using the CP/MAS method in a magnetic field of 9.4 T or more for an analysis time of three days or longer.
(Analysis Conditions)
Apparatus: Avance III 600 available from Bruker Corporation
Probe used: 4 mm MAS BB WB VT probe available from Bruker Corporation
$^{29}$Si Resonance frequency: 119.2 MHz
MAS spinning speed: 12 kHz (±5 Hz)
Analysis mode: CP/MAS
90° pulse width: 3.5 µs
Delay time: 8 sec
Observation temperature: 303 K
External reference material: silicone rubber (chemical shift: −22.3 ppm)

Example

General 2D NMR analysis was performed using a pulse sequence in which a technique for recoupling of some homonuclear interactions was applied before and after a 2D evolution period, and only DQ coherences in the 2D evolution period were selected by phase cycling.
(Analysis Conditions)
Apparatus: Avance NEO 400 available from Bruker Corporation
Probe used: 4 mm DNP-MAS BB WB LT probe available from Bruker Corporation
$^{29}$Si Resonance frequency: 79.5 MHz
MAS spinning speed: 5 kHz (±10 Hz)
Analysis mode: CP/MAS
90° Pulse width: 3.5 µs
Delay time: 8 sec
Observation temperature: 100 K
External reference material: silicone rubber (chemical shift: −22.3 ppm)

In the analysis of the comparative example, the spectrum shown in the upper part of FIG. 3 was obtained, but the peak of Q4' was buried so that the silica in a state chemically bonded to a silane-coupling agent could not be observed. In contrast, in the 2D NMR analysis of the example, the 2D $^{29}$Si-$^{29}$Si homonuclear solid-state nuclear magnetic resonance spectrum shown in FIG. 3 was obtained and Q4' (silica in a state bonded to a silane-coupling agent) could be directly observed.

Exemplary embodiments of the present disclosure include:

Embodiment 1. A chemical bond evaluation method including evaluating the presence or absence of a chemical bond between silica and a silane coupling agent in a rubber composition containing a rubber component, the silica, and the silane coupling agent.

Embodiment 2. The chemical bond evaluation method according to Embodiment 1, wherein the rubber composition contains a vulcanizing agent and a vulcanization accelerator.

Embodiment 3. The chemical bond evaluation method according to Embodiment 1 or 2, wherein the rubber composition is at least one of an unvulcanized rubber composition or a vulcanized rubber composition.

Embodiment 4. The chemical bond evaluation method according to any one of Embodiments 1 to 3, wherein the presence or absence of the chemical bond is evaluated by multidimensional solid-state nuclear magnetic resonance.

Embodiment 5. The chemical bond evaluation method according to Embodiment 4, wherein $^{29}$Si solid-state nuclear magnetic resonance is used in at least one dimension of the multidimensional solid-state nuclear magnetic resonance.

The invention claimed is:

1. A chemical bond evaluation method comprising the steps of:

performing multidimensional solid-state nuclear magnetic resonance (NMR) analysis on a rubber composition comprising a rubber component, a silica, and a silane coupling agent by using the multidimensional NMR apparatus;

using $^{29}$Si solid-state nuclear magnetic resonance, as at least part of the multidimensional NMR apparatus, in at least one dimension of the multidimensional solid-state nuclear magnetic resonance;

generating an NMR spectrum, wherein in the NMR spectrum, a vertical axis represents a $^{29}$Si DQ chemical shift axis and a horizontal axis represents a $^{29}$Si SQ chemical shift axis;

evaluating a presence or absence of a chemical bond between the silica and the silane coupling agent in the rubber composition according to the generated NMR spectrum; and detecting a cross peak representing the silica in a state forming a chemical bond with the silane coupling agent in the NMR spectrum based on the interaction between the vertical axis represents the $^{29}$Si DQ chemical shift axis and the horizontal axis represents the $^{29}$Si SQ chemical shift axis.

2. The chemical bond evaluation method according to claim 1, wherein the rubber composition comprises a vulcanizing agent and a vulcanization accelerator.

3. The chemical bond evaluation method according to claim 1, wherein the rubber composition is at least one of an unvulcanized rubber composition or a vulcanized rubber composition.

* * * * *